United States Patent [19]

Kyuma et al.

[11] 4,062,893
[45] Dec. 13, 1977

[54] PROCESS FOR PREPARING N,N-DIALKYL AROMATIC AMINES

[75] Inventors: Tatsuo Kyuma; Mikio Nakazawa, both of Kyoto, Japan

[73] Assignee: New Japan Chemical Company, Limited, Japan

[21] Appl. No.: 662,592

[22] Filed: Mar. 1, 1976

[30] Foreign Application Priority Data

Mar. 5, 1975 Japan .................................. 50-27455

[51] Int. Cl.² ............................................. C07C 87/62
[52] U.S. Cl. .................................................... 260/577
[58] Field of Search ......................................... 260/577

[56] References Cited

U.S. PATENT DOCUMENTS 3,217,040   11/1965   Schmerling ........................ 260/577

OTHER PUBLICATIONS

Groggins, "Unit Processes in Organic Synthesis," Fifth Edition, pp. 850–852, (1958).
Houben-Weyl, "Methoden der Organischen Chemie," Band XI/1, pp. 134–138, (1957).

Primary Examiner—Daniel E. Wyman
Assistant Examiner—John J. Doll
Attorney, Agent, or Firm—McGlew and Tuttle

[57] ABSTRACT

A process is provided for preparing an N,N-dialkyl aromatic amine by reacting an aromatic amine of the formula

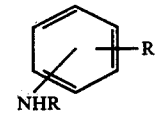

wherein R is a hydrogen atom or a lower alkyl group with a lower alcohol in the presence of at least one catalyst selected from sulfuric acid and compounds being capable of forming sulfuric acid during the reaction. The essential features of this process are characterized by:

1. maintaining the reaction temperature at 170° to 230° C,
2. maintaining the reaction system at a pressure not higher than 10 Kg/cm² gauge and capable of keeping the reaction phase liquid, and
3. feeding the amine and alcohol starting materials to the reaction system already containing at least one of the amine starting material and N,N-dialkyl aromatic amine, the desired product, and withdrawing the resulting reaction product and unreacted lower alcohol from the system in the form of a vapor while maintaining the above-mentioned pressure.

10 Claims, 1 Drawing Figure

PROCESS FOR PREPARING N,N-DIALKYL AROMATIC AMINES

BACKGROUND OF THE INVENTION

1. Field of the Invention

This invention relates to a process for preparing N,N-dialkyl aromatic amines, and more particularly to a process for preparing N,N-dialkyl aromatic amines from an aromatic amine and a lower alcohol.

2. Prior Art

It is well known to produce an N,N-dialkyl aromatic amine from an aromatic amine and a lower alcohol by liquid-phase method or gas-phase method.

With the liquid-phase method, the reaction is conducted in the presence of a liquid catalyst such as sulfuric acid. In order to cause the starting materials to be present in liquid phase for the liquid-phase reaction, in other words, to facilitate the reaction in liquid phase, it is necessary to use as the liquid phase a lower alcohol in excess, usually in at least three times the amount of aromatic amine, and to conduct the reaction at a very high pressure. In fact, "Unit Processes in Organic Synthesis," (1952, published by McGraw Hill), page 830, for example, discloses that the reaction between 1 mole of aniline and 3.2 moles of methanol in the presence of 0.1 mole of sulfuric acid requires a high pressure of 37 to 39 kg/cm$^2$. Therefore, with the liquid-phase method which requires a high pressure, it is essential to conduct the reaction in a closed reactor which must be highly resistant to pressure and corrosion because a very corrosive mineral acid is used as catalyst. Consequently, the method involves disadvantageous restrictions on the type and material of the apparatus used. The method further has the drawback of necessitating an additional step in which the reaction mixture is neutralized with an alkali to separate the desired product from the liquid phase. This entails another drawback that is becomes almost impossible to regenerate the mineral acid catalyst.

With the gas-phase method, the reaction is effected in gas phase in the presence of a solid acid catalyst of the silica of silica-alumina type. Although this mode of reaction of preferable, the solid acid catalyst, which has very high catalytic activity in the initial stage of reaction, becomes deteriorated in these characteristics as the reaction proceeds. In 20 hours, for example, the catalytic activity lowers to 80% based on the first activity, and it is therefore impossible to continue the reaction for a prolonged period of time. The cause for the deterioration of catalytic activity, while remaining yet to be fully clarified, appears to be the deposition of tar on the solid acid catalyst. However, a method has not been developed for effectively preventing or remedying the deterioration of catalytic activity, and a useful method of regeneration of the catalyst has yet to be explored.

OBJECTS OF THE INVENTION

An object of this invention is to provide a process for preparing N,N-dialkyl aromatic amines which employs sulfuric acid as a catalyst but which is free of the drawbacks of conventional liquid-phase method.

Another object of this invention is to provide a process for preparing N,N-dialkyl aromatic amines in high yields with use of sulfuric acid as a catalyst.

Another object of this invention is to provide a process for preparing N,N-dialkyl aromatic amines in which the reaction can be carried out continuously for a prolonged period of time with use of sulfuric acid as a catalyst.

Other features and objects of this invention will become apparent from the following description.

DESCRIPTION OF EMBODIMENTS OF THE INVENTION

Figure 1:
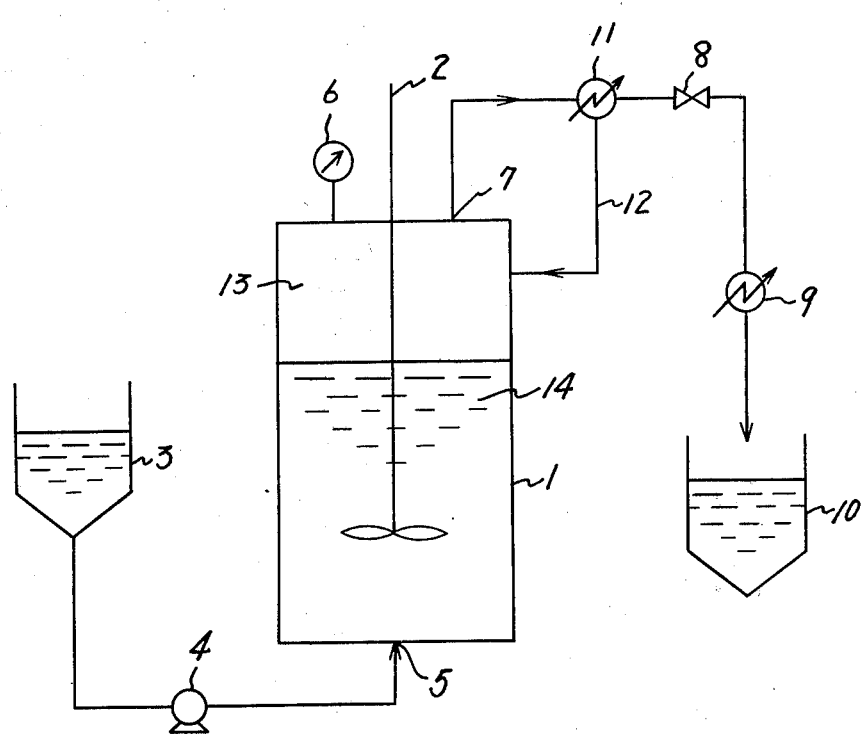

This invention provides a process for preparing and N,N-dialkyl aromatic amine by reacting an aromatic amine of the formula

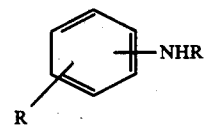
(I)

wherein R is hydrogen atom or lower alkyl with a lower alcohol in the presence of at least one catalyst selected from sulfuric acid and compounds being capable of forming sulfuric acid during a reaction (hereinafter referred to as "sulfuric acid"

1. maintaining the reaction temperature at 170° to 230° C,
2. maintaining the reaction system at a pressure not higher than 10 kg/cm$^2$ gauge and capable of keeping the reaction phase liquid, and
3. feeding the amine and alcohol starting materials to the reaction system already containing at least one of the amine starting material and/or N,N-dialkyl aromatic amine, the desired product, and withdrawing the resulting reaction product and unreacted lower alcohol from the system in the form of a vapor while maintaining the above-mentioned pressure.

We have carried out research on the process for preparing N,N-dialkyl aromatic amine by reacting an aromatic amine with a lower alcohol in the presence of sulfuric acid and found that the reaction proceeds smoothly when conducted by (1) maintaining the reaction temperature at 170° to 230° C, (2) maintaining the reaction system at a pressure not higher than 10 kg/cm$^2$ gauge and capable of keeping the reaction phase liquid, and (3) feeding the amine and alcohol starting materials to the reaction system already containing the amine starting material and/or N,N-dialkyl aromatic amine, the desired product, and withdrawing the resulting reaction product and unreacted lower alcohol from the system in the form of a vapor while maintaining the above-mentioned pressure. We have also found that because the reaction product, i.e., N,N-dialkyl aromatic amine is withdrawn from the system in the form of a vapor, there is no need to separate the amine product from the liquid catalyst. Thus the reaction consumes little or no catalyst and does not require any alkali for neutralization.

The aromatic amine used as a starting material in this invention is represented by the formula

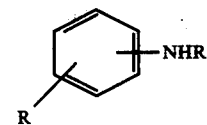

wherein R is hydrogen atom or lower alkyl. Examples of such amines are aniline, toluidine, xylidine, ethylaniline and like alkyl-substituted anilines, N-methylaniline, N-ethylaniline and like N-monoalkylanilines, N-methyltoluidine, N-ethylxylidine, N-methyl-ethylaniline, N-methylxylidine, N-ethyltoluidine, N-ethyl-ethylaniline and like N-monoalkyl-alkyl-substituted anilines, among which preferable are aniline, toluidine, xylidine, ethylaniline, N-methylaniline, N-ethylaniline, N-metyltoluidine, N-methylxylidine, N-methyl-ethylaniline, N-ethyltoluidine, N-ethylxylidine and N-ethyl-ethylaniline.

The alcohols useful in this invention are monohydric lower alcohols, preferably those having up to 5 carbon atoms. Methyl alcohol, ethyl alcohol and n-propyl alcohol are especially preferable.

Useful catalysts are sulfuric acid and compounds capable of forming sulfuric acid during the reaction. Use of hydrochloric acid is undesirable since the acid will vaporize and accompany the vapor of N,N-dialkyl aromatic amine run off. Phosphoric acid is catalytically less active than sulfuric acid and is not effective in ensuring sufficient reaction.

According to this invention, sulfuric acid may be made to be present in the reaction system from the beginning, whilst any of various compounds is likewise usable insofar as they are capable of forming sulfuric acid during the reaction. Examples of such compounds are alkyl sulfuric acid, dialkyl sulfuric acid, alkylsulfonic acid, benzenesulfonic acid, alkylbenzensulfonic acid, sulfanilic acid, alkyl-substituted sulfanilic acid, etc. Among these catalysts, sulfuric acid is most preferable.

When practicing the process of this invention, sulfuric acid, amine starting material and/or N,N-dialkyl aromatic amine, the desired product, are first placed into a reactor, and the reactor is closed. Subsequently, amine starting material and lower alcohol in a predetermined ratio are fed to the reactor at a predetermined rate, while withdrawing the desired N,N-dialkyl aromatic amine and unreacted lower alcohol with water produced by the reaction from the reactor in the form of vapor in a ratio corresponding to the above ratio and at a rate corresponding to the above feed rate. The ratio of the lower alcohol to the aromatic amine starting material may be at least the stoichiometric ratio, namely at least 2 moles, more specifically 2.5 to 10 moles, of the former per mole of the latter. Preferably, about 3 to 8 moles of the alcohol may be used per mole of the aromatic amine. The amount of catalyst to be used is 3 to 100% by weight, preferably 5 to 60% by weight, calculated as sulfuric acid based on the weight of the amine starting material and/or the desired N,N-dialkyl aromatic amine. In the present invention the amine starting material and the desired N,N-dialkyl aromatic amine may be used alone or in admixture.

In the initial stage of the reaction of this invention, an amine sulfate may possibly be precipitated depending on the kinds of amine and alcohol used, as when aniline and methanol are used in combination as starting materials. In such case, it is preferably to initiate the reaction in the presence of the same compound as the desired product. The amount of the compound to be used for this purpose may advantageously be at least 50% by weight based on the amount of the amine starting material.

Each of the aromatic amines represented by the formula (I) and the lower alcohols to be used as the starting materials are fed to the reaction system at a rate which is suitably determined in accordance with the reaction temperature, the pressure within the system, etc. Generally the feed rate is such that the apparent residence time of the amine starting material will be about 3 to 20 hours. The reaction temperature should be maintained at 170° to 230° C. If the reaction temperature is below 170° C, the reaction velocity will be low, whereas temperatures higher than 230° C are objectionable because nuclear alkyl-substituted compounds, N,N,N',N'-tetralkyl diaromatic aminomethane and like by-products will then be formed. The reaction pressure should not be higher than 10 kg/cm² gauge. If the pressure is higher than this level, the rate at which the vapor of the resulting N,N-dialkyl aromatic amine is withdrawn will be much lower than is desired, and this drawback must be remedied by increasing the alcohol charge, hence undesirable. Furthermore when conducted at a higher pressure, for example at 20 kg/cm², the reaction requires a reactor which is resistant to that pressure, e.g., 20 kg/cm². The reaction should not exceed 10 kg/cm² gauge and may preferably be about 3 to 7 kg/cm².

The feed rate of the amine starting material is such that the apparent residence time of amine will be 3 to 20 hours.

The aromatic amine obtained as the desired product is withdrawn at a rate corresponding to the feed rate of the amine starting material. Similarly the unreacted lower alcohol and water are withdrawn at a rate corresponding to the feed rate of the alcohol.

Thus according to this invention, the amine and lower alcohol starting materials are fed, in a specified ratio and at a specified rate, to the reactor already containing sulfuric acid and the amine starting material and/or the desired aromatic amine product, while withdrawing the reaction product and lower alcohol with water produced by the reaction from the reactor in a form of vapor at a rate corresponding to the feed rate. By maintaining the internal pressure of the reaction system at an appropriate constant level not higher than 10 kg/cm², the amount of lower alcohol present in the liquid phase is determined for the reaction. Although the amount of lower alcohol in the liquid phase is small at a low pressure of up to 10 kg/cm², the amount of amine starting material present in the liquid phase is similarly small, with the result that the amount of alcohol relative to the amine starting material is sufficient to effect the reaction.

Whereas it is not always required in this invention to continuously feed the amine and lower alcohol starting materials and to continuously withdraw the desired product, water and unreacted alcohol, continuous feed and withdrawal are preferable.

This invention will be described below in greater detail with reference to the accompanying drawing, FIG. 1, which is a flow chart showing a mode of practicing this invention.

According to this invention, sulfuric acid serving as a catalyst is first charged into a reactor 1 already containing amine starting material and/or N,N-dialkyl aromatic amine, the desired product. The reactor 1 is then closed and heated. Before closing the reactor 1, the air within the reactor may be replaced by an inert gas such as nitrogen or carbon dioxide gas to prevent the amine from oxidation. A stirrer 2 disposed within the reactor 1 is operated, and an aromatic amine and alcohol, the starting materials, are sent out from a tank 3 and fed to an inlet 5 of the reactor by a pump 4. The amine and alcohol may be fed from the same tank in a specified ratio or from separate tanks (not shown) individually.

When the internal pressure of the reactor 1 has reached a predetermined level as is indicated on a pressure gauge 6 on the reactor, the vapor within the reactor 1 is gradually drawn off by means of a valve 8 connected via an outlet 7 to the reactor 1, while suitably controlling the reaction conditions such as reaction temperature and amine and alcohol charges so that the internal pressure of the reactor will be maintained at a level not higher than 10 kg/cm² gauge and capable of keeping the reaction phase liquid. The internal pressure is controlled by valve 8.

When the reaction is conducted under the foregoing conditions, the amine charged in will be almost totally consumed by the reaction in the liquid-phase portion and thereby converted to dialkylamine, with the result that the amine product, excess alcohol and the water produced by the reaction form the liquid-phase portion 14 in accordance with the mole fraction ratio in inverse proportion to the respective vapor pressures. Because alcohol and water are higher than dialkylamine in vapor pressure, the liquid phase contains very small amounts of alcohol and water. On the other hand, the gas-phase portion 13 has a composition based on the mole fraction ratio and respective saturated vapor pressures of the components of the liquid-phase portion, and withdrawal of the gas-phase portion allows the reaction to proceed. Because the acid serving as the catalyst has under the reaction conditions a much lower vapor pressure than the other components of the liquid phase, the amounts of the acid in the gas phase are extremely small, so that the amounts of the acid withdrawn from the reaction system are almost negligible.

The vapor run off from the reactor 1 through the outlet 7 and then passed through a partially condenser 11 and valve 8 is further sent to a cooling unit 9, in which the vapor is condensed. The condensate is led to a tank 10. Preferably, the vapor may be withdrawn in such manner that a constant amount of liquid reaction phase will be maintained. At constant reaction temperature and pressure, the amount of product withdrawn increases with the increase in the ratio of alcohol charge to amine charge until the amount of withdrawal exceeds the charge, consequently reducing the amount of liquid phase. In such event, the ratio of alcohol to amine charge may be altered, or the reaction temperature, pressure, etc., may be suitably controlled within the foregoing ranges of reaction conditions, or the condenser 11 provided between the outlet 7 and the valve 8 may be operated to partially condense N,N-dialkyl aromatic amine, the high-boiling desired product, and to return the condensate from the condenser to the reactor 1 via a return line 12 for the control of the amount of liquid phase. Conversely, the amount of liquid phase increases with the decrease in the ratio of alcohol charge to amine charge. In this case, the amount of vapor discharge can be increased by increasing the alcohol charge relative to the amine charge, whereby the liquid phase is controllable to a reduced amount. The reaction can be carried out continuously for a prolonged period of 500 to 1,000 hours without entailing any changes in the yield and by-product.

The reaction mixture withdrawn is distilled to recover the alcohol first and then to separate off the water, whereby the desired product of this invention, i.e., N,N-dialkyl aromatic amine can be obtained.

When high-boiling by-products which are objectionable to the reaction have accumulated in the liquid phase due to a prolonged period of reaction, the operation is discontinued, and the liquid phase is taken out, neutralized and washed with water. The oily layer containing the high-boiling by-products is then distilled to recover the desired product.

This invention will be described below with reference to examples.

EXAMPLE 1

Into a 1.5-liter autoclave having a glass lining, a feed inlet and a vapor outlet and equipped with a stirrer, 500 g of N,N-dimethylaniline and 50 g of sulfuric acid are placed. After replacing the air within the autoclave by nitrogen, reaction is effected by continuously feeding aniline and methanol to the autoclave with heating and stirring at 1,000 r.p.m., while continuously withdrawing the reaction mixture from the autoclave. The reaction conditions are given below.

| | |
|---|---|
| Reaction temperature: | 200± 10° C. |
| Pressure: | 5 kg/cm² gauge. |
| Feed rate of aniline: | 35 g/hr. |
| Methanol/aniline feed ratio (mole ratio): | 5.5–6.5. |

When analyzed by gas chromatography, the reaction mixture withdrawn over a period of 200 hours after the initiation of the reaction is found to be composed of 0.4% by weight of N-methylaniline, 99.6% by weight of N,N-dimethylaniline and up to 0.01% by weight of compounds having a methylated benzene ring, exclusive of water and methanol. By-products other than the above and unreacted aniline are undetectable. The reaction mixture is distilled to remove water and methanol, whereby 9,100 g of N,N-dimethylaniline having a purity of 99.6% is obtained.

On the other hand, the mixture remaining in the autoclave is drawn off, neutralized, washed with water and distilled to remove water and obtain 480 g of crude substance. When separated from a high-boiling fraction by vacuum distillation, the crude substance gives 450 g of N,N-dimethylaniline having a purity of 99.6%. Conversion of aniline: 100%. Yield based on aniline: 99.0%.

Even after 200 hours' reaction, no changes are found in the yield and by-products. The excess of methanol can be recovered by distillation almost in a stoichiometric amount.

EXAMPLE 2

The same procedure as in Example 1 is repeated except that o-toluidine is used in place of aniline and that 500 g of o-toluidine, 50 g of sulfuric acid and 10 g of methanol are charged into the autoclave. The reaction conditions are as follows.

| | |
|---|---|
| Reaction temperature: | 200 ± 10° C. |
| Pressure: | 6 kg/cm² gauge. |
| Feed rate of o-toluidine: | 50 g/hr. |
| Methanol/o-toluidine feed ratio (mole ratio): | 5–6. |

The reaction mixture withdrawn over a period of 200 hours after the start of the reaction and the mixture remaining in the autoclave are each treated in the same manner as in Example 1 to obtain N,N-dimethyl-o-toluidine (yield based on o-toluidine: 98.8%). The reaction mixture is obtained upon the lapse of the 200 hours and is found to be composed of 0.2% by weight of N-methyl-o-toluidine, 99.8% by weight of N,N-dimethyl-o- toluidine and not more than 0.01% by weight of compounds having a methylated benzene ring, exclusive of water and methanol. The mixture is found free from any unreacted o-toluidine.

EXAMPLE 3

The same procedure as in Example 1 is repeated except that ethanol is used in place of methanol and that 500 g of N,N-diethylaniline and 93 g of sulfanilic acid are charged into the autoclave. The reaction conditions are as follows:

| | |
|---|---|
| Reaction temperature: | 200 ± 10° C. |
| Pressure: | 6 kg/cm² gauge. |
| Feed rate of aniline: | 30 g/hr. |
| Ethanol/aniline feed ratio (mole ratio): | 5-6. |

The reaction mixture withdrawn over a period of 200 hours after the start of the reaction and the mixture remaining in the autoclave are each treated in the same manner as in Example 1 to obtain N,N-diethylaniline (yield based on aniline: 99.1%). The above-mentioned reaction mixture is found to be composed of 0.4% by weight of N-ethylaniline, 99.6% by weight of N,N-diethylaniline and not more than 0.02% by weight of compounds having an ethylated benzene ring, exclusive of water and ethanol. No unreacted aniline is detected.

EXAMPLE 4

The same procedure as in Example 1 is repeated except that the amines and lower alcohols listed in Table 1 below are reacted under the reaction conditions indicated in Table 1 to obtain corresponding N,N-dialkyl aromatic amines. Table 2 shows the results, i.e., the amine conversion as determined by the analysis of the reaction mixture derived from 200 hours' reaction and the yield of N,N-dialkyl aromatic amine (based on the amine starting material).

Table 1

| | Materials | | Reaction conditions | | | |
|---|---|---|---|---|---|---|
| No. | Amine | Alcohol | Pressure (kg/cm² gauge) | Temperature (° C) | Alcohol/amine feed ratio (mole ratio) | Amine feed rate (g/hr.) |
| 1 | 2,4-Xylidine | Methanol | 3 | 220 ± 10 | 5- 6 | 60 |
| 2 | o-Ethylaniline | Methanol | 5 | 220 ± 10 | 5 - 6 | 55 |
| 3 | N-Methylaniline | Methanol | 3 | 220 ± 10 | 5 - 6 | 25 |
| 4 | N-Ethylaniline | n-Propanol | 3 | 220 ± 10 | 5 - 6 | 50 |

Table 2

| | Results of reaction | |
|---|---|---|
| No. | Conversion of amine (%) | Yield of N,N-dialkyl aromatic amine (%) |
| 1 | 100 | 98.7 |
| 2 | 100 | 99.1 |
| 3 | 100 | 98.5 |
| 4 | 100 | 99.5 |

What we claim is:

1. Process for preparing an N,N-dialkyl aromatic amine which comprises subjecting an aromatic amine of the formula

wherein R is a hydrogen atom or a lower alkyl group, to reaction with a lower alcohol in the presence of at least one catalyst selected from the group consisting of (a) sulfuric acid and (b) compounds capable of forming sulfuric acid during the reaction process, in a suitable vessel, maintaining the reaction at a temperature of about 170° to about 230° C, maintaining the reaction pressure at a pressure not higher than about 10 kg/cm² gauge which is capable of keeping the reaction phase liquid, and feeding the amine and alcohol starting materials to the reaction system in said vessel already containing at least one of the amine starting materials and N,N-dialkyl aromatic amine, the desired product, and withdrawing the resulting reaction product and unreacted lower alcohol from the system in the form of a vapor while maintaining the above-mentioned pressure.

2. The process for preparing an N,N-dialkyl aromatic amine according to claim 1, in which said pressure is 3 to 7 kg/cm² gauge.

3. The process for preparing an N,N-dialkyl aromatic amine according to claim 1, in which said amine starting material to be fed is charged at feed rate so that the apparent residence time of amine will be 3 to 20 hours.

4. The process for preparing an N,N-dialkyl aromatic amine according to claim 1, in which said lower alcohol is used at a ratio of 2.5 to 10 moles per mole of the amine starting material.

5. The process for preparing and N,N-dialkyl aromatic amine according to claim 4, in which said ratio is about 3 to 8 moles per mole of the amine starting material.

6. The process for preparing an N,N-dialkyl aromatic amine according to claim 1, in which said aromatic amine is at least one species selected from the group consisting of aniline, toluidine, xylidine, ethylaniline, N-methylaniline, N-ethylaniline, N-methyltoluidine, N-methylxylidine, N-methyl-ethylaniline, N-ethyltoluidine, N-ethyxylidine and N-ethylethylaniline.

7. The process for preparing an N,N-dialkyl aromatic amine according to claim 1, in which said alcohol is at least one species selected from the group consisting of methyl alcohol, ethyl alcohol and n-propyl alcohol.

8. The process for preparing an N,N-dialkyl aromatic amine according to claim 1, in which said compounds being capable of forming sulfuric acid during the reaction is at least one species selected from the group consisting of alkyl sulfuric acid, dialkyl sulfuric acid, alkylsulfonic acid, benzenesulfonic acid, sulfanilic acid, alkyl-substituted sulfanilic acid.

9. The process for preparing N,N-dialkyl aromatic amine according to claim 1, in which said catalyst is sulfuric acid.

10. The process for preparing an N,N-dialkyl aromatic amine according to claim 1, in which said catalyst is used in an amount of 3 to 100% by weight calculated as sulfuric acid based on the weight of the amine starting material and/or the desired N,-N-dialkyl aromatic amine.

* * * * *